United States Patent [19]

Ogura

[11] Patent Number: 5,046,483
[45] Date of Patent: Sep. 10, 1991

[54] APPARATUS FOR DISINTEGRATING CALCULUSES

[75] Inventor: Ichiro Ogura, Yokohama, Japan

[73] Assignee: Kabushiki Kaisha Toshiba, Kawasaki, Japan

[21] Appl. No.: 483,648

[22] Filed: Feb. 23, 1990

[30] Foreign Application Priority Data

Feb. 28, 1989 [JP] Japan .................................. 1-47201

[51] Int. Cl.$^5$ ............................................. A61B 17/22
[52] U.S. Cl. .............................................. 128/24 OEL
[58] Field of Search ........ 128/24 EL, 24 AA, 660.01, 128/660.03, 662.03, 804

[56] References Cited

U.S. PATENT DOCUMENTS

| 4,237,901 | 12/1980 | Taenzer | 128/660.07 |
| 4,338,190 | 7/1982 | Kraus et al. | |
| 4,517,985 | 5/1985 | Teslawski et al. | 128/660.01 |
| 4,803,995 | 2/1989 | Ishida et al. | 128/660.03 |
| 4,811,725 | 3/1989 | Grasser | 128/24 A |
| 4,893,614 | 1/1990 | Takayama et al. | 128/24 A |

FOREIGN PATENT DOCUMENTS

| 0131654 | 1/1983 | European Pat. Off. | 128/24 A |
| 0090138 | 10/1983 | European Pat. Off. | 128/24 A |
| 0265741 | 5/1988 | European Pat. Off. | 128/24 A |
| 3503702 | 8/1986 | Fed. Rep. of Germany | 128/24 A |
| 3544707 | 6/1987 | Fed. Rep. of Germany | 128/24 A |

Primary Examiner—Ruth S. Smith
Attorney, Agent, or Firm—Oblon, Spivak, McClelland, Maier & Neustadt

[57] ABSTRACT

An apparatus for disintegrating calculuses of the type found in a human body, transmits a shockwave through a container filled with a liquid medium, into the body. The apparatus comprises a tank which stores the liquid, a sensor for detecting pressure in the container, and a liquid control system. When pressure exceeds a preset value, the control system transports liquid from the container to the tank until the pressure falls below the preset value.

11 Claims, 3 Drawing Sheets

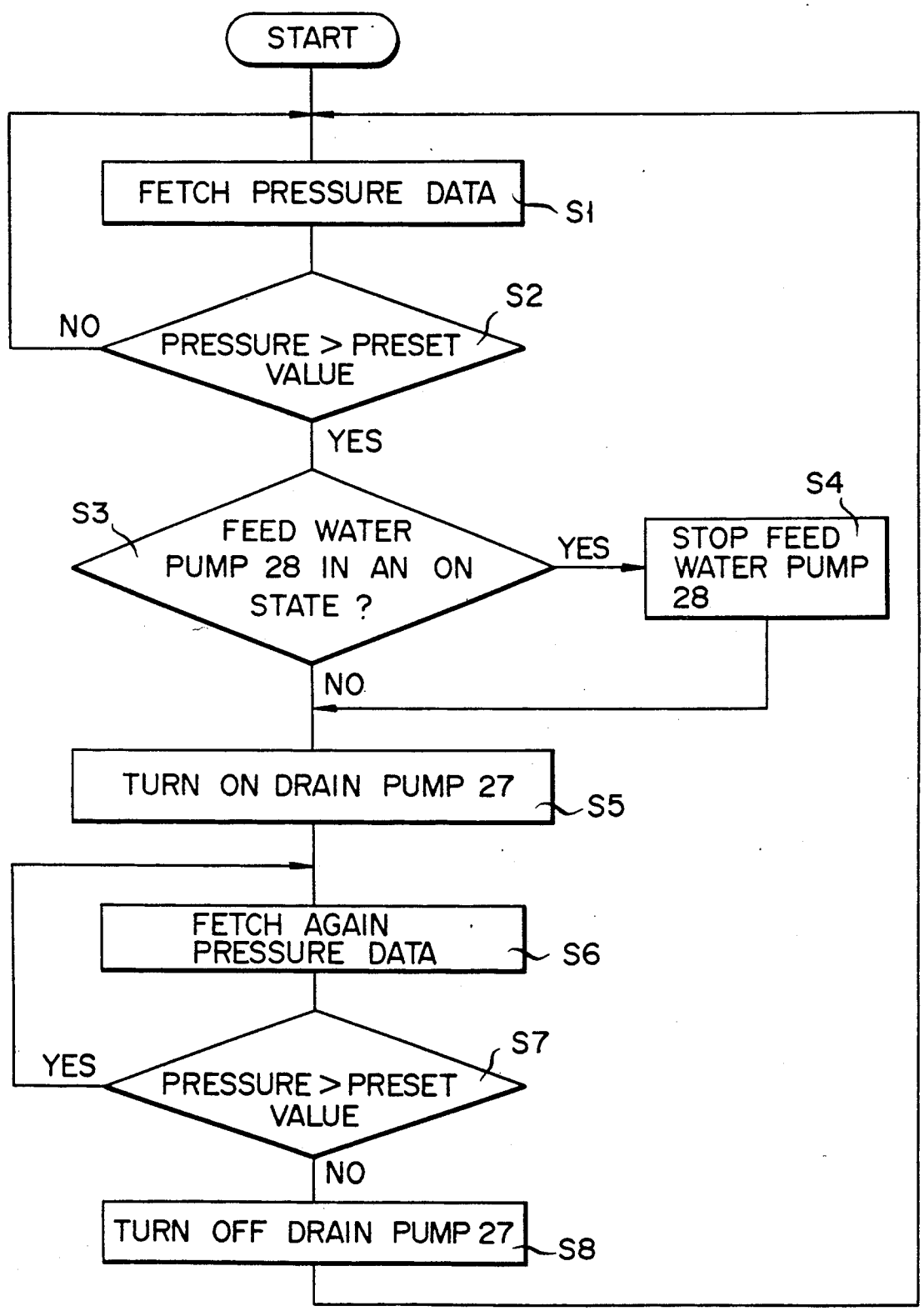
F I G. 2

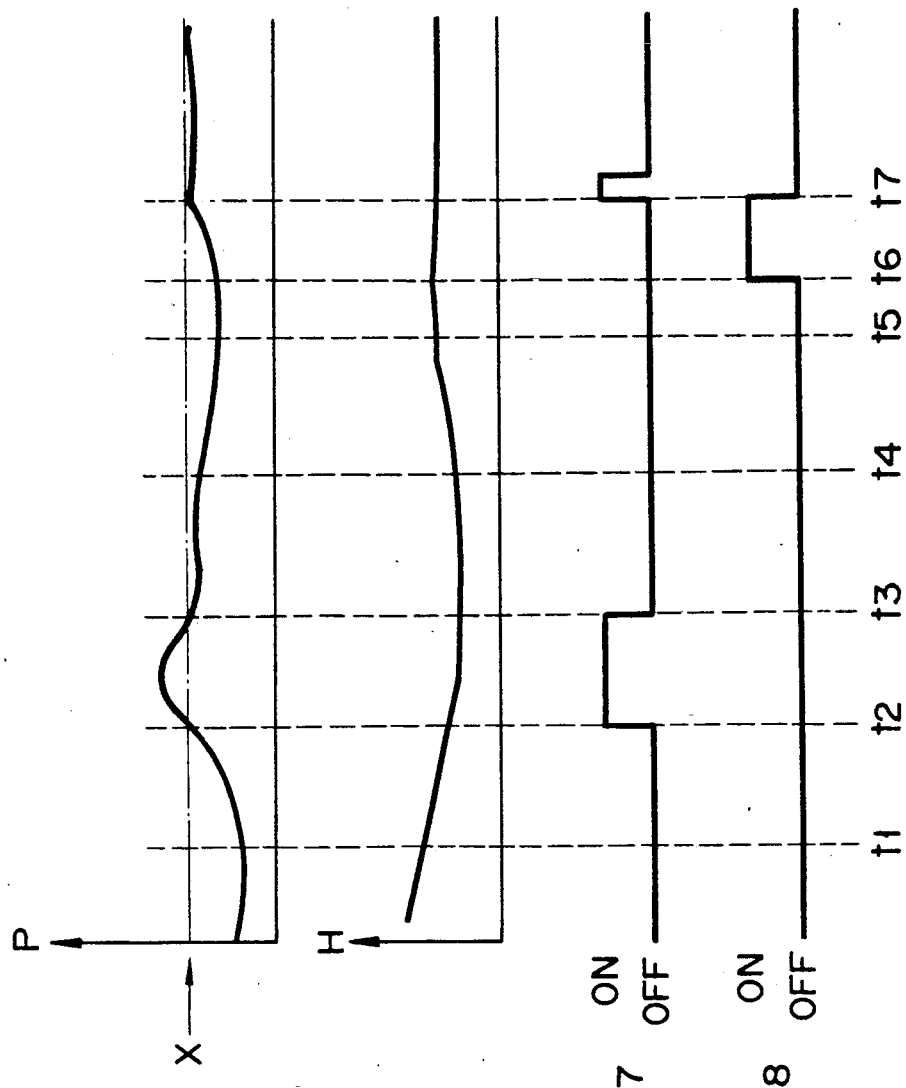

APPARATUS FOR DISINTEGRATING CALCULUSES

BACKGROUND OF THE INVENTION

1. Field of the Invention

The present invention relates to an apparatus for disintegrating calculuses of the type in which a calculus in a human body of a patient is disintegrated with a disintegrating energy of a shock wave externally applied.

2. Description of the Related Art

The calculus disintegrating apparatus using the disintegrating energy of a shock wave for disintegrating a calculus or calculuses in a human body have been developed as an apparatus for curing a disease by renal calculus or gallstone without surgical operations. In this type of apparatus, a shock wave is generated by making use of an electric spark or ultrasonic wave oscillation, and a calculus to be desintigrated in a human body is irradiated with the shock wave. To effectively irradiate the calculus with the shock wave, it is required that no air layer exists in a propagating path of the shock wave (i.e., between a shock wave generator and the body surface of a patient). The reason for this is that the air layer impedes propagation of the shock wave within the human body because, the wave is reflected by the air layer. This requirement may be readily satisfied by filling the propagation path with a liquid medium, e.g., water. There have been known two specific approaches to realize this. In a first method, a shock wave generator is placed in a bath tub filled with water. A patient is sunk into the bath tub. Under this condition, the shock wave is radiated toward the patient through the water. In a second method, an expandable container such as a rubber bag filled with the liquid is disposed in the front of a shock wave generator. The container is made to closely contact the body of a patient, before the shock wave is radiated. The shock wave generator and the container form an applicator. In the second method, a patient need not to sink into the bath tub. In this respect, mental and physical strain on a patient is lessened.

It is desirable that the applicator is disposed above a patient laid on the bed. The reason for this is that the direction of shock wave radiation may be readily checked, and that an operation of the applicator resembles that of a conventional medical apparatus, such as an X-ray apparatus and an ultrasound diagnostic apparatus, and therefore such a layout of the applicator above the patient allows an operator, e.g., a doctor, to be easily accessible to the applicator. With the layout of the applicator above the patient, when the applicator is positioned to focus the shock wave generator on the calculus, an operator may mistakenly move the applicator down to far, or supply an excessive amount of liquid medium into the applicator. Consequently, a patient is strongly pressed against the bed. In other words, where the position of the applicator and the amount of the liquid are both proper, the patient may be comfortably subjected to treatment, without any feeling of the weight of the applicator and the liquid. On the other hand, where the position of the applicator or amount of liquid is improper, the applicator strongly presses the patient against the bed. Under this condition, the patient feels uncomfortable, and in an extreme case, he has difficulty in breathing, and he may suffer a fracture due to excessive pressure.

SUMMARY OF THE INVENTION

Accordingly, an object of the present invention is to provide an apparatus for disintegrating calculuses which protects a patient from an excessive pressure applied by the applicator. Excessive pressure may be caused by the drain pump and/or the feed water pump operating improperly or being operated by mistake.

To achieve the above object, there is provided an apparatus for disintegrating calculuses of the type in which a calculus in a human body of a patient is disinetegrated with a shock wave generated by a shock wave generator which is transmitted through a liquid medium in an expandable rubber bag container, the liquid medium allowing the shock wave to propagate therethrough. The apparatus comprising: a tank for storing the liquid medium; a pressure sensor for detecting pressure in the applicator; and liquid control means. When detected pressure exceeds a preset value, the liquid control means drains the liquid medium from the container, filling the tank, till the detected pressure drops below the preset value. When the detected pressure exceeds the preset value during the supply of the liquid from the tank to the applicator; the liquid control means stops the supply of the liquid and starts draining the liquid.

Because the applicator is hermetically closed, pressure in the applicator, particularly pressure in an upper part of the liquid within the applicator, acts as a negative pressure in accordance with a depth of the liquid, when the apparatus is operated for calculus treatment. Under this condition, if the applicator is pressed against the patient or the amount of the liquid is increased, the pressure within the applicator increases and inclines towards a positive pressure. The "preset value" is set at a pressure value at which a patient begins to uncomfortably feel the weight of the applicator. When the pressure within the applicator is above the preset value, the liquid is drained from the applicator to drop the pressure. When the liquid is being supplied to the applicator, the supply of the liquid is stopped when the drainage of the liquid starts. The problems of the uncomfortable feeling and difficulty in breathing are successfully eliminated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 2 is a flowchart showing a sequence of control steps by a control circuit of the apparatus of FIG. 1.

FIGS. 3A to 3D form a timing chart useful in explaining an operation of the apparatus of FIG. 1.

DETAILED DESCRIPTION OF THE PREFERRED EMBODIMENTS

Figure 1:
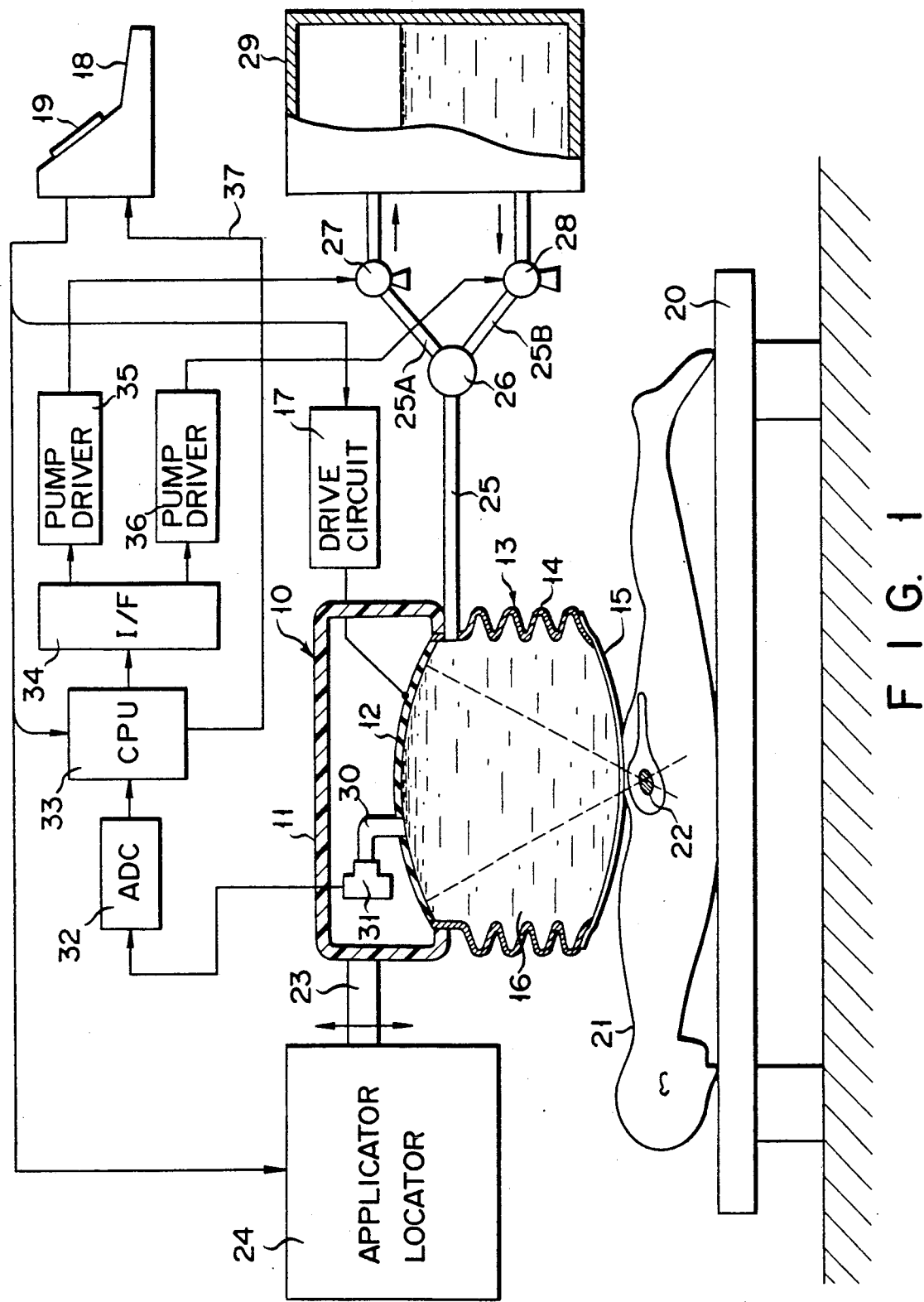
FIG. 1 shows in block and schematic form an arrangement of an apparatus for calculuses disintegration according to an embodiment of the present invention.

A preferred embodiment of the present invention will be described with reference to the accompanying drawings.

FIG. 1 shows in block and schematic form an arrangement of an apparatus for calculuses disintegration according to an embodiment of the present invention In the figure, the applicator 10 is comprised of a tubular support 11 opened at the bottom (as viewed in the drawing), a shock wave generator 12, and an expandable rubber bag container 13. The generator 12 is shaped like a spherical shell having a plurality of ring-shaped piezoelectric elements of different diameters which are concentrically arrayed. The generator 12 is mounted on the support 11, closing the opening of the support 11. The rubber bag container 13 includes a bellows 14 and a contact thin film 15, which comes in contact with the body surface of a patient 21 on a bed 20 when he takes medical treatment. The top of the bellows 14 is located in the front of the shock wave generator 12, and is supported by the support 11. The contact thin film 15, is a rubber film, for example, and is fixed to the bottom of the bellows 14. The inside of the container 13, viz., a space defined by the shock wave generator 12, bellows 14, and contact film 15, is filled with liquid 16 allowing a shock wave to propagate. The liquid 16 is preferably degased water. When treatment is made, an operator, e.g., a doctor, instructs emission of a shock wave on a console 18. By the instruction, a drive circuit 17 is driven to apply a pulse voltage to the shock wave generator 12. In response to the pulse, the shock wave generator 12 generates or emits a shock wave. The shock wave propagates through the liquid 16 and the contact film 15, and hits a calculus 22 in a human body of the patient 21.

The support 11 is coupled with an applicator locator 24 by means of a support arm 23. In response to an instruction entered from the console 18, the locator 24 vertically moves the applicator 10 as in the direction of the arrow. One end of a pipe 25 is communicably joined with the rubber bag 13. The pipe 25 is bifurcated at the middle into branch pipes 25A and 25B by means of a branching means 26. A drain pump 27 and a feed water pump 28 are inserted in the branch pipes 25A and 25B, respectively. The ends of the branch pipes 25A and 25B, which are respectively opposite to those connecting to the branching means 26, are communicably coupled with a tank 29. The tank 29 stores the degased liquid 16, such as water.

A pressure transfer pipe 30 is communicably connected at one end with the top of the rubber bag container 13, while the other end is connected with a pressure sensor 31. The pressure sensor 31 generates an electrical signal whose amplitude depends on pressure within the pipe 30, viz., pressure within the container 13. The pressure sensor 31 may be any suitable known semiconductor pressure sensor. An output signal of the sensor 31 is digitized by an A/D converter (ADC) 32, and is applied to a CPU (central processing unit) 33. The CPU 33 compares an output digital signal of the ADC 32 (which is indicative of a pressure sensed by the sensor 31) with a present valve. On the basis of the comparison result and the on- and off-states of the pumps 27 and 28, the CPU 33 drives through an interface 34 pump drivers 35 and 36 for driving the drain pump 27 and the feed water pump 28.

A control flow of the CPU 33 is as illustrated in FIG. 2. At the start of treatment, the CPU 33 fetches pressure data collected by the sensor 31, that is, reads a digital signal outputted from the ADC 32 (step S1). In step S2, the CPU 33 checks if the pressure data > a preset value. When the answer is YES, the CPU checks whether the feed water pump 28 is operating or is in an on state, in step S3. Of course, the CPU 33 has known the present state of the pump 28, on- or off-state. If the pump 28 is in an on state, the CPU 33 stops a signal supplied to the pump driver 36 and turns off pump 28, in step S4. Then, it proceeds to step S5. In step S5, the CPU 33 sends a signal to the pump driver 35, to turn on the drain pump 27. In the next step S6, the CPU 33 reads a pressure sensed by the pressure sensor 31 as in step S1, and checks if the pressure is greater than the preset value, in step S7. If the answer is YES, the CPU 33 returns to step S6. If the answer is NO, it goes to step S8. In this step, the CPU 33 stops the signal to the pump driver 35, thereby turning off the drain pump 27. After departing from step S8, the CPU 33 returns to step S1, and repeats the similar sequence of processings.

An operation of the apparatus for disintegration of calculuses thus arranged will be described with reference to FIGS. 3A through 3D. FIG. 3A shows a variation of pressure "P" within the container 13 that is sensed by the sensor 31; FIG. 3B, a variation of height "H" of the contact film 15; FIG. 3C, on- and off-states of the drain pump 27; FIG. 3D, on- and off-states of the feed water pump 28.

Returning to FIG. 1, there is illustrated how to disintegrate the renal calculus 22 by using the calculus disintegrating apparatus under discussion. As shown, the patient 21 lies on his face on the bed 20. The applicator 10 is previously positioned above a kidney of the patient 21 by the applicator locator 24. Before treatment, the contact thin film 15 is not in contact with the patient 21. Under this condition, a space is created under the contact thin film 15. Accordingly, the pressure sensor 31 detects a negative pressure. This state continues until time point t1 when the applicator 10 is dropped by the locator 24 and comes in contact with the patient 21.

When the contact film 15 contacts the patient 21 at time t1, the pressure within the container 13 detected by the sensor 31 gradually increases, and reaches a preset value "X" at time t2. The preset value "X" is a pressure, i.e., 0 kg/cm$^2$, at which the patient 21 begins to uncomfortably feel the pressure applied from the applicator 10 or to feel the weight of the liquid 16. When the pressure reaches the preset value "X" at time t2, the CPU 33 operates the drain pump 27 to cause it to start drainage of the liquid 16 from the rubber bag container 13 to the tank 29. Then, the pressure in the container 13 gradually decreases. At time t3, when the pressure drops below the preset value "X", the CPU 33 stops the drain pump 27 again. As the result of such operation, the patient 21 feels little weight from the applicator 10, and may undergo comfortable treatment.

At time t4, in response to an instruction by an operator, the applicator locator 24 is driven and the applicator 10 starts to lift. At time t5, the contact film 15 disengages from the patient 21, and at time t6, the operator enters an instruction of starting up the feed water pump 28 from the console 18. In turn, the the pump 28 starts up its operation, and starts to supply the liquid 16 to the container 13. Accordingly, the pressure within the container 13 starts to increase. When a proper amount of the liquid 16 is reached within the container 13, the operator enters an instruction to stop the pump 28. Accordingly, such pressure as to make the patient irritative or uncomforted will never be applied to the patient. When the pump stop instruction is not entered, the increase of the container pressure continues and at time t7, the pressure exceeds the preset value "X". The excessive pressure is applied through the sensor 31 and the ADC 32 to the CPU 33. In turn, the CPU 33 turns on the drain pump 27 again, to reduce the pressure within the container 13. In this case, if the feed water pump 28 is turned off at this time t7, a time that the patient feels the pressure from the applicator 10 is reduced, and the reduction of the patient's pressure feeling time brings about better results.

In this way, the CPU 33 turns on the drain pump 27 when the pressure within the container 13 is in excess of the preset value "X", and turns off the pump 27 when the pressure is below the preset value. When the pressure > the preset value, if the feed water pump 28 is operating, the CPU 33 turns on the drain pump 27 while at the same time turns off the feed water pump 28. Through the controls by the CPU, the patient 21 may undergo treatment while being free from the uncomfortable pressure from the applicator 10. Further, if the applicator locator 24, for example, is mistakenly operated or improperly operates, the patient 21 can be protected from the resultant danger. With the controls by the CPU, the positioning of the applicator 10 by the operator and the adjustment of the amount of the liquid 16 in the container are made easy. Although the operator is under continuing pressure to keep the pressure applied from the applicator to the patient 21 below a preset value, the present invention releases the operator from such strain.

In this embodiment, the CPU 33 generates an alarm signal 37 during a period that the pressure sensed by the sensor 31 is above the preset value. The alarm signal 37 is sent to the console 18, and is visually presented by a display 19 on the console 18. The alarm may be generated acoustically by means of a speaker. From the alarm, the operator recognizes that the uncomfortable pressure is being applied to the patient 21 and may enter a proper instruction on the console.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for disintegrating calculuses of the type in which a calculus in the body of a patient is disintegrated by means of a shock wave, comprising:
    means for generating a shock wave;
    expandable container means for housing a liquid medium and coupled to the shock wave generating means to allow the shock wave to propagate therethrough;
    means for storing said liquid medium;
    pressure detecting means for detecting pressure in said expandable container means; and
    liquid control means for, when the detected pressure exceeds a preset value, draining the liquid medium from said expandable container means to said storing means until the detected pressure drops below the preset value.

2. The apparatus according to claim 1, wherein said shock wave generating means includes at least one piezoelectric element, which produces the shock wave in response to a voltage pulse.

3. The apparatus according to claim 1, wherein said expandable container means includes a bellows having first and second openings, the first opening being enclosed by said means for generating, and the second opening being enclosed by a contact film which is adapted to come into contact with the surface of the patient's body.

4. The apparatus according to claim 1, wherein said pressure detecting means includes a pressure transfer pipe communicably coupled at one end with the top surface of said container means, and a pressure sensor coupled with the other end of said pipe for producing an electric signal in accordance with the pressure in said expandable container means.

5. The apparatus according to claim 1, further comprising means for vertically moving said shock wave generating means and said container means above the patient.

6. The apparatus according to claim 1, further comprising means for generating an alarm signal during a period when said detected pressure exceeds the preset value.

7. An apparatus for disintegrating calculuses of the type in which a calculus in the body of a patient is disintegrated by means of a shock wave, comprising:
    means for generating a shock wave;
    expandable container means for housing a liquid medium and coupled to the shock wave generating means to allow the shock wave to propagate therethrough;
    means for storing the liquid medium;
    pressure detecting means for detecting pressure in said expandable container means; and
    liquid control means for said liquid medium, which when the detected pressure exceeds a preset value, drains said liquid medium from said expandable container means to said storing means until said detected pressure drops below the preset value, and stops supply of the liquid medium from said storing means to said container means and starts drainage of said container means when the detected pressure exceeds the preset value during supply of the liquid medium.

8. The apparatus according to claim 7, wherein said liquid control means includes a pipe coupled at a first end to said container means and bifurcated at the middle into two branch pipes whose second ends are coupled to said storing means, a first pump attached to one of said branch pipes for draining the liquid medium from said container means into said storing means, and a second pump attached to the other branch pipe for supplying the liquid medium in said storing means to said container means.

9. The apparatus according to claim 7, wherein said liquid control means includes a pipe coupled at a first end to said container means and bifurcated at the middle into two branch pipes whose second ends are coupled to said storing means, a first pump inserted in one of said branch pipes for draining the liquid medium from said container means into said storing means, and a second pump inserted in the other branch pipe for supplying the liquid medium in said storing means to said container means, means for, when detected pressure exceeds the preset value, turning on said first pump until said detected pressure drops below a preset value, and means for stopping said second pump and starting up said first pump when the detected pressure exceeds the preset value during the on-state of said second pump.

10. The apparatus according to claim 7, further comprising means for vertically moving said shock wave generating means and said container means above said patient.

11. The apparatus according to claim 7, further comprising means for generating an alarm signal during a period when said detected pressure exceeds the preset value.

* * * * *